Figure 1:
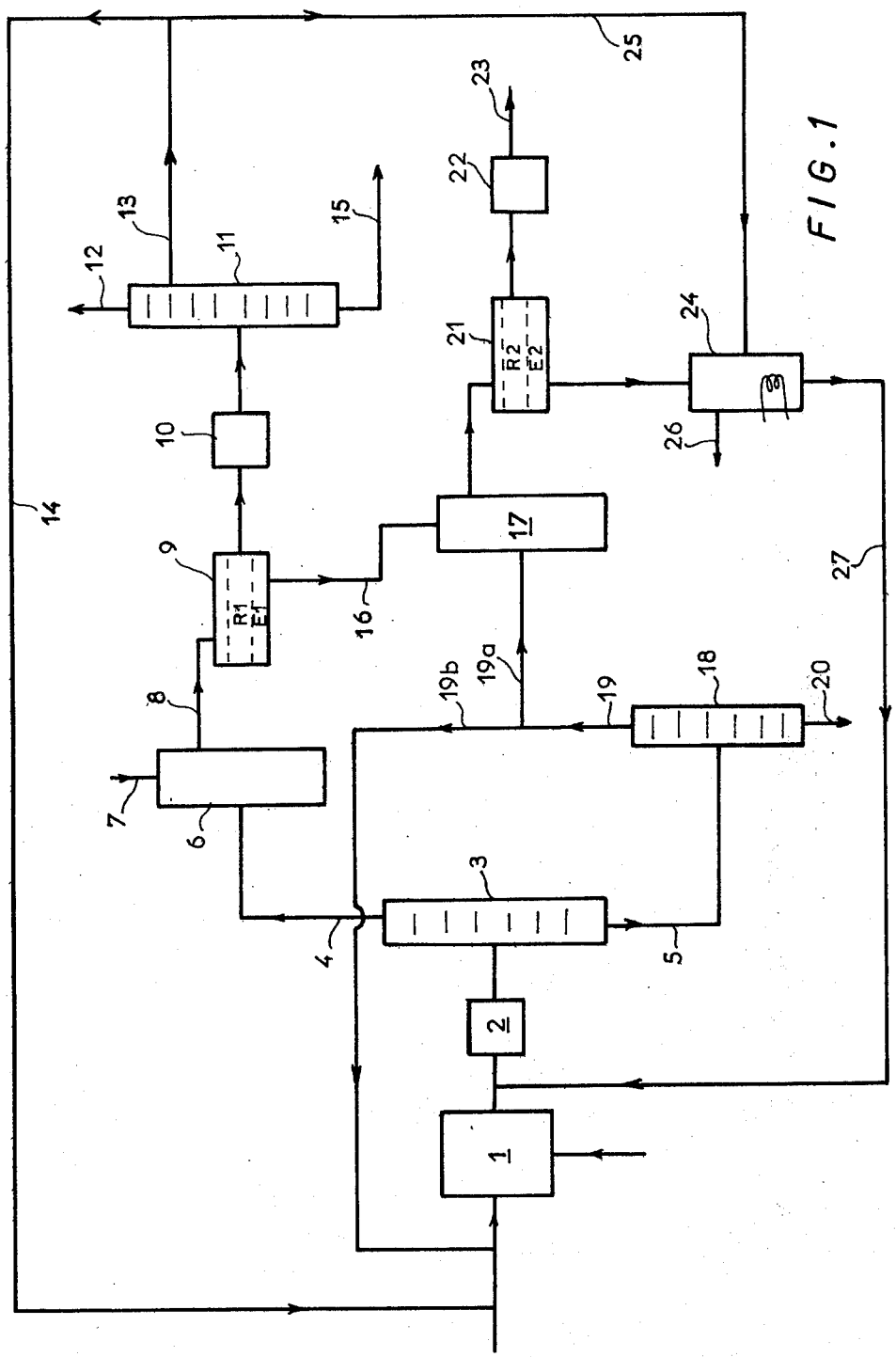

United States Patent [19]

Henrich et al.

[11] 3,962,366
[45] June 8, 1976

[54] ISOMERIZATION AND SEPARATION OF CYMENES FROM MIXTURES CONTAINING SAME

[75] Inventors: Gaston Henrich, Saint-Avold; Philippe Gillet, Creutzwald, both of France

[73] Assignee: Societe Chimique des Charbonnages, Courbevoie, France

[22] Filed: Aug. 5, 1974

[21] Appl. No.: 495,000

[30] Foreign Application Priority Data

Aug. 9, 1973    France .............................. 73.29188

[52] U.S. Cl. .................. 260/674 A; 260/668 A; 260/671 P; 260/672 T; 260/674 SE
[51] Int. Cl.² .................. C07C 7/01; C07C 15/02
[58] Field of Search ...... 260/674 SE, 674 A, 668 A, 260/672 T, 671 P

[56] References Cited
UNITED STATES PATENTS

| | | | |
|---|---|---|---|
| 2,727,078 | 12/1955 | Shoemaker .......................... | 260/674 |
| 2,741,647 | 4/1956 | McCaulay et al. ................... | 260/668 |
| 2,770,662 | 11/1956 | McCaulay et al. ................... | 260/668 |
| 2,795,632 | 6/1957 | McCaulay et al. ................... | 260/671 |

*Primary Examiner*—Delbert E. Gantz
*Assistant Examiner*—C. E. Spresser
*Attorney, Agent, or Firm*—Karl W. Flocks

[57] ABSTRACT

The invention concerns an improvement in the process of isomerization and separation of ortho-, meta- and para-cymenes from mixtures containing same by contacting said mixtures with HF and BF₃ at low temperatures in order to form a preferential complex with the meta-cymene, said improvement comprising the steps of:

a. contacting the mixture to be treated containing the ortho-, meta- and para-cymenes with 4 to 50 molecules of HF for 1 mol of total cymenes and 0.5 to 3 mols of BF₃ for 1 mol of metacymene present in this mixture;

b. controlling of the rates of isomerization governed by the following equations (1), (2), and (3)

o-cymene    m-cymene $\rightleftarrows$ 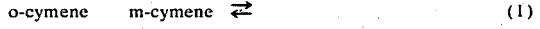 (1)

o-cymene    p-cymene $\rightleftarrows$ . 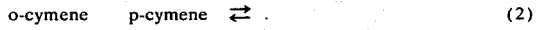 (2)

p-cymene    m-cymene $\rightleftarrows$ 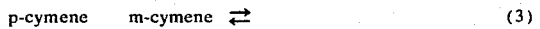 (3)

and the rate of the following transalkylation reaction (4)

2 cymenes $\rightleftarrows$ 1 toluene + 1 di-isopropyl-toluene 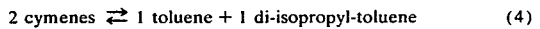 (4)

by utilizing both low temperatures between a temperature lower than −50°C. and a temperature lower than −5°C. and toluene added;

c. allowing the reaction medium resulting from steps (a) and (b) to decantate in order to obtain two phases, an upper phase or raffinate fraction containing the ortho- and para-cymenes and a lower phase comprising the complex of meta-cymene in solution in HF;

d. separating the said two phases coming from step (c) and e. treating each phase coming from the step (d) in order to isolate and recover the desired ortho-, meta- and para-cymenes.

9 Claims, 3 Drawing Figures

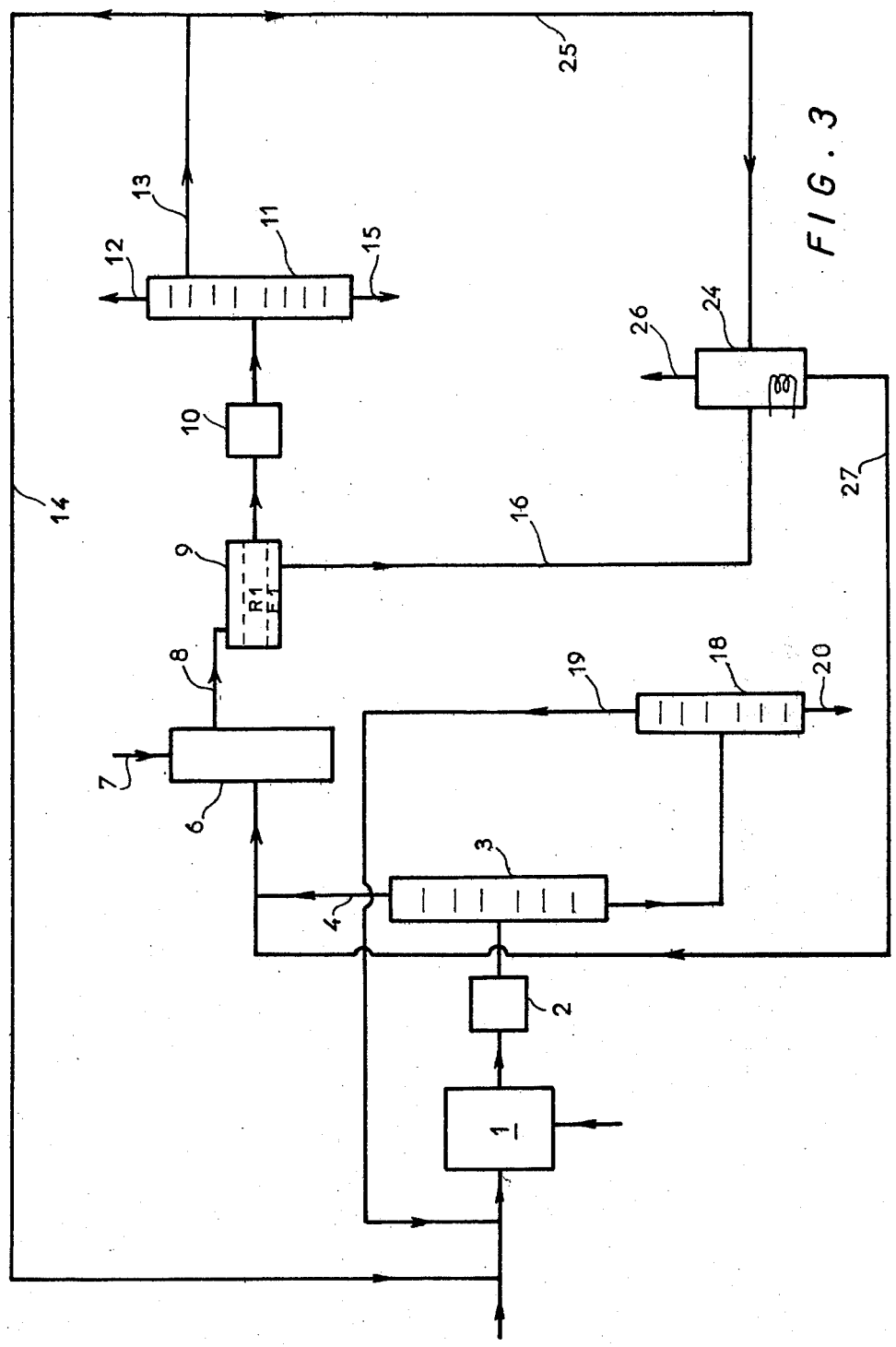

ISOMERIZATION AND SEPARATION OF CYMENES FROM MIXTURES CONTAINING SAME

The present invention relates to a process for isomerizating and separating cymenes (ortho, meta and para) from mixtures containing these compounds.

Cymenes are especially employed in the production of cresols by peroxidation of these hydrocarbons, followed by heterolytic decomposition of the peroxides obtained. The cymenes themselves are generally obtained by the Friedel-Crafts reaction of propylene (or of hydrocarbon cuts containing same) on toluene (or on hydrocarbon cuts containing same).

This reaction supplies a mixture which generally comprises, in addition to other possible hydrocarbons deriving from the starting reactants, the three isomers of cymene in the proportion of 2 to 4% of the ortho isomer, 60 to 64% of the meta isomer, and 32 to 36% of the para isomer. As the separation by crystallization of the meta- and para-cresols obtained from such a mixture is complicated and costly, it has preferably been sought to separate the corresponding cymenes. However, the vicinity of the boiling points and the formation of azeotropes render this separation extremely difficult, at least in the case of the proportions of the meta and para isomers indicated above, these proportions corresponding to the thermo-dynamic equilibrium.

Now, the Applicants have provided a process for izomerizing and separating cymenes which implies the formation of a complex by means of the mixture HF - $BF_3$.

It is known that aromatic hydrocarbons such as xylene form a complex with hydrofluoric acid and boron trifluoride. When the boron trifluoride is injected into a stirred mixture of HF and hydrocarbons at low temperatures, the $BF_3$ is absorbed. After decantation of the reaction medium, two phases are obtained:

an upper phase (so called raffinate) containing saturated hydrocarbons and aromatic hydrocarbons having the lowest basicity;

a lower phase constituted by the complex in solution in HF and containing the aromatic hydrocarbon or hydrocarbons having the highest basicity.

Thus, it is possible to extract from a mixture of aromatic hydrocarbons the most basic hydrocarbon, and to extract from a mixture of aromatic isomers the meta isomer which is the most basic (in particular the m-xylene in the case for example of a mixture of xylene isomers). From the resultant complex constituting the lower phase, it is possible to isolate the pure meta isomer by thermal decomposition of the complex. The ortho and para xylenes are then separated by known means, such as distillation.

Now, when it is desired to apply this method to cymenes, difficulties are encountered which are not appreciably met with in the case of xylenes, due to the fact that the reactions of isomerization and transalkylation (following the below equilibrium equations) take place in the presence of the mixture HF - $BF_3$ at ambient temperature and even at temperatures lower than 0°C., towards −15° or −20°C., until the thermo-dynamic equilibrium proportions indicated above are reached:

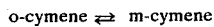
$$\text{o-cymene} \rightleftarrows \text{m-cymene} \quad (1)$$

$$\text{o-cymene} \rightleftarrows \text{p-cymene} \quad (2)$$

$$\text{p-cymene} \rightleftarrows \text{m-cymene} \quad (3)$$

$$2 \text{ cymenes} \rightleftarrows 1 \text{ toluene} + 1 \text{ di-isopropyltoluene} \quad (4)$$

Thus, when a preferential complex is formed with meta-cymene, following the known technique, the supernatant raffinate portion has a tendency to become isomerized so as to give back a mixture corresponding to the thermo-dynamic equilibrium, which makes it impossible to isolate the pure para-cymens. Furthermore, the thermal decomposition of the meta-cymene complex HF-$BF_3$ is also accompanied by isomerization and transalkylation which make it impossible to obtain pure meta-cymene.

Now the Applicants have discovered a process which makes it possible at will, from a mixture of isomers of cymene, either to isolate these latter in the porportion corresponding to the thermo-dynamic equilibrium in which they are present in this mixture, or to enrich this latter in one or the other of these isomers in order to extract and isolate it subsequently, thus overcoming the drawbacks referred to above.

In order to do this, the Applicants make use simultaneously of two means, namely:

a. The temperature at which is effected the formation reaction of the complex with HF - $BF_3$ in such manner as to facilitate or on the contrary to inhibit the isomerization reactions;

b. and the use of toluene in such manner as to inhibit the transalkylation reaction and to displace the equilibrium of the reaction (4) above from the right towards the left.

As regards the temperature, the Applicants have in fact found that by working at temperatures such that these are located in the advantageous range defined by $-40°C < t < -5°C$ the production of meta-cymene was facilitated, and that by working at temperatures lower than −45°C and preferably lower than −50°C, the production of para-cymene was facilitated. In this way therefore, the more the temperature is reduced, the more the isomerization of the ortho and para-cymenes to meta-cymene is strongly reduced.

In addition, the operation carried out in the presence of toluene results in inhibition of the transalkylation reaction (4). It results that by acting simultaneously on these two factors, the isomerization of cymenes can be directed and orientated at will and therefore the desired isomer can be obtained after its extraction from the medium.

The process according to the invention is thus characterized by the fact that a complex is formed in the mixture comprising the cymenes by means of HF and $BF_3$ at low temperature and in the presence of toluene, that the proportions of isomerization are controlled by acting on the temperature, and that the transalkylation is orientated by means of the toluene, that the upper phase or raffinate containing the ortho and para-cymenes and the lower phase constituted by the meta-cymene complex in solution in HF are separated, and that the constituents of each of these phases are isolated.

As regards the isolation of the o- and p-cymenes present in the raffinate, this isolation can be effected by distillation.

On the contrary, with respect to the isolation of the meta-cymene present in the complex of the lower phase, a thermal decomposition (as in the case of the separation of meta-xylene from its complex with HF and BF₃) would not be profitable since, leading to the partial isomerization of the m-cymene to o- and p-cymenes, it would result in a substantial loss of m-cymene.

In order to overcome this disadvantage, the invention provides, for the recovery of the m-cymene from its complex with HF and BF$_3$, the displacement of the m-cymene by a compound of greater basicity, preferably di-isopropyl-toluene. In order to do this, the complex is contacting at low temperature with the said more basic compound and after decantation, two phases are obtained:

a raffinate phase containing the m-cymene;
and a complex phase containing the said basic compound (di-isopropyl-toluene).

This new complex phase may then be advantageously decomposed by heat in the presence of toluene, which, in the case of di-isopropyl-toluene, facilitates the transalkylation of the di-isopropyl-toluene to cymenes (reaction (4) above) which can be sent back to the treatment cycle.

In accordance with other features:

The quantity of HF which is utilized for the formation of the complex is comprised between 4 and 50 molecules for one molecule of cymene (total cymenes);

the quantity of BF$_3$ which is used for the formation of the complex is from 0.5 to 1 mol per mol of initial meta-cymene in the case in which it is desired to obtain mainly meta-cymene and from 1.5 to 3 mols per mol of initial meta-cymene in the case where it is desired mainly to obtain para-cymene.

It will be noted that when the mixture contains more than 90% of para-cymene, the separation meta-para by distillation becomes possible (the meta passing over first), and can yield para-cymene at 99%.

The invention making it possible to separate the isomers of cymene, it will also be noted that they are used for the production of cresols: ortho-cymene gives either orthocresol which is easy to separate, or decomposition products which can also be separated.

Other features and advantages of the invention will be brought out more clearly in the description which follows:

1. Extraction and isolation of m-cymene from a mixture containing the three isomers o-, m- and p-.

The mixture is brought while stirring into contact with HF and BF₃ in a proportion of 17 mols of HF and 1 mol of BF₃ for 1 mol of m-cymene in the presence of toluene, at a temperature lower than −50°C.

The result is:

a. that at this temperature, the isomerization reactions are very strongly reduced;

b. that the presence of toluene displaces the equilibrium 2 cymenes ⇌ toluene + di-IPT from the right towards the left (di-isopropyltoluene).

It is also possible to operate in the presence of a saturated hydrocarbon, which may aid selectivity.

After separation of the phases, there is thus obtained a raffinate containing of the order of 95% of para-cymene (referred to the sum of the meta + para), which raffinate can easily be distilled in order to separate-out and collect the constituents.

The complex with a base of meta-cymene which is obtained is brought into contact at low temperature (not above −40°C) with di-IPT which are more basic than the meta-cymene. As already indicated above, there are obtained:

the raffinate phase containing the meta-cymene;
the complex phase containing the di-IPT.

The raffinate phase is distilled in order to recover from it the m-cymene at a purity of 99%.

With regard to the new complex form, this can be thermally decomposed in the presence of toluene, which facilitates the transalkylation of the di-IPT to cymenes which are sent back to the treatment cycle.

The purity of 99% resulting from the conditions indicated above permits a direct utilization of the m-cymene obtained for the purpose for example of peroxidation, without distillation or supplementary fractionation.

It is known to displace the m-cymene by decomposition of the complex, working for example according to the method described in the U.S. Pat No. 2,741,647, but the decomposition of the complex obtained by this method at a temperature between −5°C. and +5°C only results in a purity of the m-cymene of about 86%, this this latter being separated with difficulty or inseparable from its isomers by distillation and being utilizable directly only with difficulty.

There is given below a comparative Table of the results of decomposition of the complex, effected respectively at −43°C and at −5°C.

|  | Test at −43°C. | Test at −5°C. |
|---|---|---|
| Analysis of the complex containing meta-cymene: |  |  |
| Toluene | 35.10 | 39.43 |
| m-cymene | 63.05 | 57.27 |
| p-cymene | 0.37 | 0.07 |
| o-cymene | 0.02 | traces |
| di-IPT | 0.27 | 2.07 |
| m-cymene/cymenes total | 99.4 | 99.8 |
| Mols of di-IPT engaged per mol of m-cymene | 2.2 | 2.2 |
| Duration of test | 1 hour | 1 hour |
| Analysis of the raffinate portion after treatment: |  |  |
| Toluene | 16.26 | 17.06 |
| m-cymene | 41.82 | 40.39 |
| p-cymene | 0.34 | 5.71 |
| o-cymene | 0.04 | 0.67 |
| di-IPT | 25.15 | 35.32 |
| m-cymene/cymenes total | 99.1 | 86.3 |

2. Isomerization to m-cymene or enrichment of a mixture of cymenes in m-cymene

The operation is again carried out in the presence of toluene in order to prevent transalkylation (reaction 4), but this time working is carried out at a higher temperature than in the previous case (between −5° and −20°C, for example) in order to facilitate the isomerization of the ortho- and para-cymenes of the raffinate portion to m-cymene. The complex with a base of m-cymene is treated as before (displacement by di-IPT at −50°C. followed by thermal decomposition in order to recover the m-cymene. The raffinate portion is recycled and again complexed.

3. Isomerization to o- and p-cymene, or enrichment of a mixture of cymenes in o- and p-cymene The operation is carried out in the presence of toluene and at low temperature (−60°C) in order to prevent transalkylation and isomerization, the quantity of $BF_3$ being 3 mols and that of HF being 20 mols per mol of m-cymene in the mixture.

The complex with a base of m-cymene is decomposed by heat in order to cause partial isomerization, and in the presence of toluene (in order to prevent transalkylation). The residuary hydrocarbon phase (a mixture of toluene and the 3 isomers of cymene) is re-cycled.

The raffinate portion only contains the o- and p-isomers which can be separated from the raffinate portion by distillation.

Figure 2:
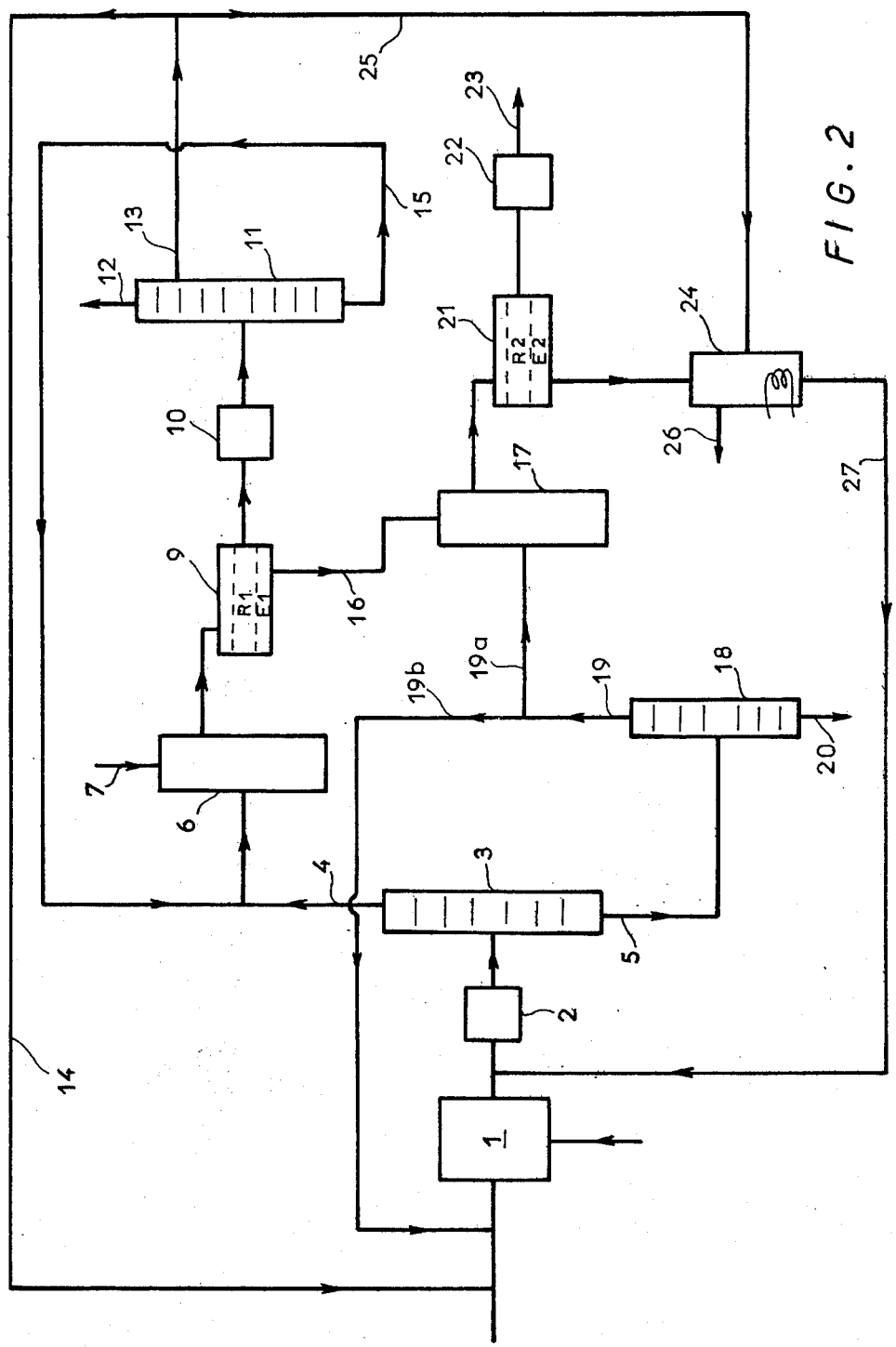

The accompanying FIGS. 1 to 3, illustrate in the form of diagrams and by way of explanation only without any restrictive sense, one advantageous form of application of the process of the invention applied to the product coming directly from the manufacturing unit of the cymenes.

This separation stage can thus be integrated with the manufacturing stage of the cymenes. The alkylates of the first stage contain essentially for example a fraction in $C_7$ (toluene + non-aromatic) enriched in non-aromatics with respect to the supply mixture with $C_7$ of cymenes, of di-isopropyl-toluenes (di-IPT) and heavy products. These alkylates thus coming from the alkylator 1 (supplied with $C_7$ and $C_3$ cuts) are neutralized at 2 and are then sent into the column 3, from which there is extracted, from the head 4, the $C_7$ and the cymenes, from the bottom 5, the di-IPT and the heavy products which are sent for separation into the column 18 from which there are extracted, at the head through 19, the di-IPT and from the bottom through 20, the heavy products.

A - Separation of the isomers (FIG. 1)

The head fraction containing the cymenes is treated in the reactor 6 with HF and $BF_3$ (admitted at 7), at a temperature lower than −60°C. The toluene present in the fraction subjected to the treatment prevents the transalkylation reaction, while the non-aromatics increase the selectivity.

The mixture of the raffinate portion and the complex is extracted from the reactor 6 through the conduit 8 and is then decanted at 9.

The raffinate portion $R_1$ containing the non-aromatics, the toluene and the isomers o- and p-cymenes, is neutralized at 10 and then distilled in the column 11. From this column there is extracted from the head through the conduit 12, a fraction enriched in non-aromatics, laterally (through the conduit 13) a $C_7$ cut (which is partly re-cycled through the conduit 14 to the alkylation) and at the bottom (through the conduit 15), the isomers o- and p-cymenes.

It should be noted that the purging of the non-aromatics necessary before re-cycling in order to maintain a constant concentration of toluene at the inlet of the alkylator 1, is carried out at the level of the separation.

The complex $E_1$ with a base of m-cymene is sent through the conduit 16 into the reactor 17, at the same time as a fraction, through 19a, of the di-IPT coming from the tower 18, the other fraction being re-cycled at 1 through 19b. The mixture is kept below −60°C at 17.

After decantation at 21, there are obtained:

a raffinate portion $R_2$ containing toluene and m-cymene which is neutralized at 22 and then distilled so as to obtain the m-cymene at 23;

a complex $E_2$ which is thermally decomposed at 24 in the presence of a fraction of the mixture of $C_7$ coming through the conduits 13 and 25 from the column 11 in order to facilitate the transalkylation.

The HF and $BF_3$ collected at 26 are recycled to the reactor 6, while the hydrocarbons (toluene, non-aromatics, cymenes, di-IPT) coming from 24 are re-cycled through the conduit 27.

B - Isomerization to m-cymene (FIG. 2)

The diagram forming the subject of this figure is identical to the diagram of FIG. 1, except that working is carried out in the reactors 6 and 17 at a high temperature (−20°C for example) in order to facilitate the isomerization, and that the mixture of the o- and p-cymenes coming from 11 through the conduit 15 is re-cycled into the reactor 6.

C - Isomerization to p-cymene (FIG. 3)

In this case, the extraction from the reactor 6 is effected at below −60°C and the complex $E_1$ is thermally decomposed at 24 in the presence of the $C_7$ cut. The hydrocarbons coming from 24 are re-cycled at 6.

It will of course be understood that the present invention has only been described purely by way of explanation and not in any restrictive sense and that any useful modification may be made thereto without thereby departing from its scope as defined in the appended Claims.

We claim:

1. In the process for isomerizing and separating the ortho-, meta- and para-cymenes from mixtures containing said compounds by putting said mixtures into contact with HF and $BF_3$ at low temperatures so as to form a preferential complex with meta- cymene in the presence of toluene, the improvement comprising using a contact temperature between −5° and −60°C, separating the two resulting phases and displacing the m-cymene from said complex by contacting same with di-isopropyl toluene at a temperature not above −40°C when the initial contact temperature is from −5° to −40°C.

2. Improvement according to claim 1, wherein the mixture to be treated is contacted at a temperature between 5° and −45°C with 4 to 50 mols of HF for 1 mol of total cymenes and with 1.5 to 3 mols of $BF_3$ per mol of meta-cymene present in this mixture, the two resulting phases are separated after decantation, the upper phase containing o- and p-cymenes and substantially no m-cymene and the lower phase containing substantially all the m-cymene is thermally decomposed in the presence of toluene, whereby the m-cymene is partially isomerized into o- and p-cymenes which can be treated again as the said to be treated mixture.

3. Improvement according to claim 1, wherein the mixture to be treated is contacted at a temperature between −40°C and −5°C with 4 to 50 mols of HF for 1 mol of total cymenes and with about 0.5 to 1 mol of $BF_3$ per mol of meta-cymene present in this mixture, the two resulting phases are separated after decantation, the upper phase containing a mixture of o-, m- and p-cymenes is treated again as the said to be treated mixture and the lower phase of the m-cymene complex is contacted with di-isopropyl-toluene at a temperature not above −40°C, the resulting medium is allowed to decantate, the two resulting layers are separated, the upper layer containing substantially all the m-cymene and the lower layer containing substantially all the di-isopropyl-toluene and said upper layer is distilled whereby meta-cymene with a purity of 99% is obtained.

4. In a process for isomerizing and separating the ortho-, meta- and para-cymenes from mixtures containing said compounds by bringing a mixture of said compounds in contact with HF and $BF_3$ at low temperatures so as to form a preferential complex with meta-cymene, the improvement comprising:
   a. contacting the mixture to be treated containing the ortho-, meta- and para-cymenes with 4 to 50 mols of HF for each mol of total cymenes and 1.5 to 3 mols of $BF_3$ for each mol of meta-cymene present in said mixture, and maintaining the temperature of said mixture during said contacting at no greater than −50°C, while simultaneously contacting said mixture with added toluene;
   b. allowing the reaction medium resulting from step (a) to separate into two phases, an upper phase or raffinate fraction containing the ortho- and para-cymenes, and a lower phase comprising the complex of meta-cymene in solution in HF;
   c. separating said two phases from step (b);
   d. distilling said raffinate fraction to obtain the desired ortho- and para-cymenes; and
   e. thermally treating said lower phase to recover said HF and $BF_3$ and recycling the mixture of cymene isomers so obtained.

5. In a process for isomerizing and separating the ortho-, meta- and para-cymenes from mixtures containing said compounds by bringing a mixture of said compounds in contact with HF and $BF_3$ at low temperatures so as to form a preferential complex with meta-cymene, the improvement comprising:
   a. contacting said mixture of ortho-, meta- and para-cymenes with 4 to 50 mols of HF for each mol of total cymenes and 0.5 to 1 mol of $BF_3$ for each mol of meta-cymene in said mixture, said contacting being carried out at a temperature between −5°C and about −45°C, and in the presence of added toluene;
   b. allowing the reaction medium resulting from step (a) to separate into two phases, an upper phase of raffinate fraction containing the ortho- and para-cymenes, and a lower phase comprising the complex of meta-cymene in solution in HF;
   c. separating said two phases from step (b);
   d. distilling said raffinate fraction to obtain ortho- and para-cymenes;
   e. contacting said lower phase comprising the complex of meta-cymene in solution in HF with di-isopropyl-toluene at a temperature not greater that −40°C and thereby obtaining two phases, an upper phase containing the meta-cymene and a complex lower phase containing the di-isopropyl-toluene;
   f. recovering the meta-cymene from said upper phase and
   g. thermally treating said lower phase of the complex to recover said HF and said $BF_3$.

6. In a process for isomerizing and separating the ortho-, meta- and para-cymenes from mixtures containing said compounds by bringing a mixture of said compounds in contact with HF and $BF_3$ at low temperatures so as to form a preferential complex with meta-cymene, the improvement comprising:
   a. contacting said mixture of ortho-, meta- and para-cymenes with 4 to 50 mols of HF for each mol of total cymenes and 0.5 to 3 mols of $BF_3$ for each mol of meta-cymene in said mixture, said contacting being carried out at a temperature not greater than −50°C, and in the presence of added toluene;
   b. allowing the reaction medium resulting from step (a) to separate into two phases, an upper phase or raffinate fraction containing the ortho- and para-cymenes, and a lower phase comprising the complex of meta-cymene in solution in HF;
   c. separating said two phases from step (b);
   d. distilling said raffinate fraction to obtain the desired ortho- and para-cymenes;
   e. contacting said lower phase comprising the complex of meta-cymene in solution in HF with di-isopropyltoluene at a temperature not greater than −40°C and thereby obtaining two phases, an upper phase containing the meta-cymene and a complex lower phase containing the di-isopropyl-toluene;
   f. recovering the meta-cymene from said upper phase and
   g. thermally treating said lower phase of the complex to recover said HF and said $BF_3$.

7. In the process for isomerizing and separating the ortho-, meta- and para-cymenes from mixtures containing said compounds by putting said mixtures into contact with HF and $BF_3$ at low temperatures so as to form a preferential complex with meta- cymene in the presence of toluene, the improvement comprising
   contacting the mixture to be treated at a temperature not above −50°C with 4 to 50 mols of HF for 1 mol of total cymenes and with about 1 mol of $BF_3$ for 1 mol of meta-cymene present in this mixture, and
   separating the two resulting phases after decantation, the upper phase containing substantially all the o- and p-cymenes and the lower phase containing substantially all the m-cymene.

8. In the process for isomerizing and separating the ortho-, meta- and para-cymenes from mixtures containing said compounds by putting said mixtures into contact with HF and $BF_3$ at low temperatures so as to form a preferential complex with meta- cymene in the presence of toluene, the improvement comprising
   contacting the mixture to be treated at a temperature of −60°C with 20 mols of HF and 3 mols of $BF_3$ per mol of m-cymene in the presence of toluene,
   separating the two resulting phases after decantation, the upper phase containing o- and p-cymenes and substantially no m-cymene and the lower phase containing substantially all the m-cymene, and
   thermally decomposing the lower phase in the presence of toluene, whereby the m-cymene is partially isomerized into o- and p-cymenes which can be treated again as the said to be treated mixture.

9. In the process for isomerizing and separating the ortho-, meta- and para-cymenes from mixtures containing said compounds by putting said mixtures into contact with HF and $BF_3$ at low temperatures so as to form a preferential complex with meta- cymene in the presence of toluene, the improvements comprising
   contacting the mixture to be treated at a temperature lower than −50°C with 17 mols of HF and 1 mol of $BF_3$ per mol of m-cymene in the presence of toluene,
   separating the two resulting phases,
   distilling the upper phase containing on the order of 95% of para-cymene and recovering the same,
   contacting the lower phase containing the m-cymene complex with di-isopropyl-toluene at a temperature not above −40°C and decanting the resulting medium,
   separating the two resulting layers,
   distilling the upper layer whereby meta-cymene with a purity of 99% is recovered and the lower layer is thermally decomposed in the presence of toluene whereby the transalkylation of the di-isopropyl-toluene into cymenes is achieved said cymenes being sent back to the treatment cycle.

* * * * *